(12) United States Patent
Valiani (10) Patent No.: US 10,918,382 B2
(45) Date of Patent: Feb. 16, 2021

(54) INTRAORAL STAPLER

(71) Applicant: Shahram Valiani, Downey, CA (US)

(72) Inventor: Shahram Valiani, Downey, CA (US)

(*) Notice: Subject to any disclaimer, the term of this patent is extended or adjusted under 35 U.S.C. 154(b) by 212 days.

(21) Appl. No.: 16/249,575

(22) Filed: Jan. 16, 2019

(65) Prior Publication Data

US 2019/0142415 A1  May 16, 2019

Related U.S. Application Data

(63) Continuation-in-part of application No. 14/948,502, filed on Nov. 23, 2015, now Pat. No. 10,213,199.

(51) Int. Cl.

| A61B 17/068 | (2006.01) |
| A61B 17/064 | (2006.01) |
| A61B 17/24  | (2006.01) |
| A61B 17/072 | (2006.01) |

(52) U.S. Cl.
CPC ........ *A61B 17/068* (2013.01); *A61B 17/0644* (2013.01); *A61B 17/24* (2013.01); *A61B 2017/0645* (2013.01); *A61B 2017/0649* (2013.01); *A61B 2017/07221* (2013.01); *A61B 2017/07271* (2013.01)

(58) Field of Classification Search
CPC ................ A61B 17/068; A61B 17/105; A61B 2017/0645; A61B 17/1227; A61B 17/0682; A61B 17/24
USPC ............................ 227/175.1–182.1; 606/219
See application file for complete search history.

(56) References Cited

U.S. PATENT DOCUMENTS

| 4,887,756 A * | 12/1989 | Puchy ............... A61B 17/0644 227/19 |
| 4,997,436 A * | 3/1991 | Oberlander ......... A61B 17/064 227/901 |
| 5,222,961 A * | 6/1993 | Nakao .................... A61B 17/10 606/142 |
| 5,289,963 A * | 3/1994 | McGarry ........... A61B 17/0684 227/175.1 |
| 5,634,932 A * | 6/1997 | Schmidt ............ A61B 17/1285 606/157 |
| 7,401,720 B1 * | 7/2008 | Durrani .............. A61B 17/0682 227/109 |
| 7,533,790 B1 * | 5/2009 | Knodel ............. A61B 17/0684 227/175.1 |

(Continued)

*Primary Examiner* — Robert F Long
*Assistant Examiner* — Xavier A Madison
(74) *Attorney, Agent, or Firm* — Argus Intellectual Enterprise; Daniel Enea; Jordan Sworen (57) ABSTRACT

An intraoral surgical stapling apparatus. The intraoral surgical stapling apparatus includes a handle assembly having a trigger for actuation of a surgical staple. A barrel section extends outward from the handle assembly and includes a staple firing mechanism for loading and advancing the surgical staple in a loading position towards a forward end of the intraoral surgical stapling apparatus. A fixed body forms a channel to receive an advancing unit. The advancing unit is connected to the trigger such that a sliding plate positioned within the channel slides forward and backward by actuating the trigger. A pair of splay arms have a forward end opposite a rearward end. The forward end engages the staple and cycles through a between the loading position, a forward advancing position, and a staple open biasing position. The engaged staple is biased and configured to be applied to a tissue site.

20 Claims, 9 Drawing Sheets

(56) References Cited

U.S. PATENT DOCUMENTS 8,784,447 B2 * 7/2014 Coleman ............ A61B 17/0682
606/213
8,870,049 B2 * 10/2014 Amid ............... A61B 17/07207
227/176.1

* cited by examiner

INTRAORAL STAPLER

CROSS-REFERENCE TO RELATED APPLICATIONS

This application claims the benefit of and priority to U.S. patent application Ser. No. 14/948,502, a pending nonprovisional utility patent application, filed on Nov. 23, 2015, and the entire disclosure of which is incorporated by reference herein.

BACKGROUND OF THE INVENTION

The present invention relates to an apparatus for fastening tissue and applying a surgical staple to a tissue site. More particularly, the present disclosure relates to an intraoral surgical stapling apparatus having a loading unit capable of applying surgical staples to tissue. The present invention further provides an intraoral stapler having an advancing unit that loads, advances, and fires/prepares a staple to be applied to a tissue site in a single actuation motion.

Placing oral sutures is a difficult, time-intensive process because many areas of the mouth are difficult to reach. In addition to difficulties associated with reaching wound sites that are situated deep in the oral cavity of a patient, practitioners' movements are often restricted by the mandible and maxilla, forcing them to work at challenging or uncomfortable angles. Despite these difficulties, properly placing oral sutures is critical because sutures ensure proper healing, assist in recovery, and prevent post-surgical complications, such as dry sockets after the extraction of a tooth.

SUMMARY OF THE INVENTION

In view of the foregoing disadvantages inherent in the known types of surgical staplers now present in the known art, the present invention provides a surgical stapler configured for intraoral use. The surgical stapler includes an elongated barrel section that allows for surgical staples to be applied to difficult-to-reach locations within a patient's oral cavity. The distal end of the barrel is configured to releasably engage a plurality of spring-biased surgical staples. When actuated, the surgical stapler loads a single lowermost staple from the prearranged staples, which slides forward with a pair of splay arms. Once advanced, the distance between the splay arms increases towards their forward end, thereby gradually opening the spring-biased staple until the staple is open and ready to be applied to a tissue wound site. The user can then place the staple at the wound site. Once free from the arms of the surgical stapler, the staple then closes around the wound site. Upon release of the trigger, the splay arms return to the initial loading position to repeat the cycle of loading, advancing, and firing a single staple from the prearranged staples.

The present invention is designed for intraoral applications, improving the efficiency and convenience of closing wounds within the oral cavities of patients. Furthermore, the present invention ensures that surgical staples are applied in a consistent and reliable manner, reducing the risks associated with improperly closed wounds. Furthermore, the present invention is configured to utilize spring-biased staples that are configured to automatically close around and suture a wound site once applied thereto.

It is an objective of the present invention to provide in some embodiments, the surgical intraoral stapling apparatus including a series of prearranged staples disposed horizontally and vertically stacked in a staple cartridge toward the forward end thereof, wherein the advancing unit is configured to load a lowermost staple and prepare the staple for suturing to tissue.

It is another objective of the present invention to provide an embodiment comprising a spring biasing the pair of splay arms to a closed position and a spring biasing a bar to a loading position, respectively, such that the advancing unit and trigger return to an initial loading position upon release of the trigger.

It is therefore an object of the present invention to provide a new and improved surgical intraoral stapling apparatus that has all of the advantages of the known art and none of the disadvantages.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Reference is made herein to the attached drawings. Like reference numerals are used throughout the drawings to depict like or similar elements of the surgical intraoral stapling apparatus. For the purposes of presenting a brief and clear description of the present invention, the preferred embodiment will be discussed as used for suturing an open wound after a tooth extraction. In the description that follows, the term "rearward" or "proximal," as is traditional, will refer to the end of the surgical stapling apparatus that is closest to the operator, while the term "forward" or "distal" will refer to the end of the apparatus that is farthest from the operator. The figures are intended for representative purposes only and should not be considered to be limiting in any respect.

Figure 1:
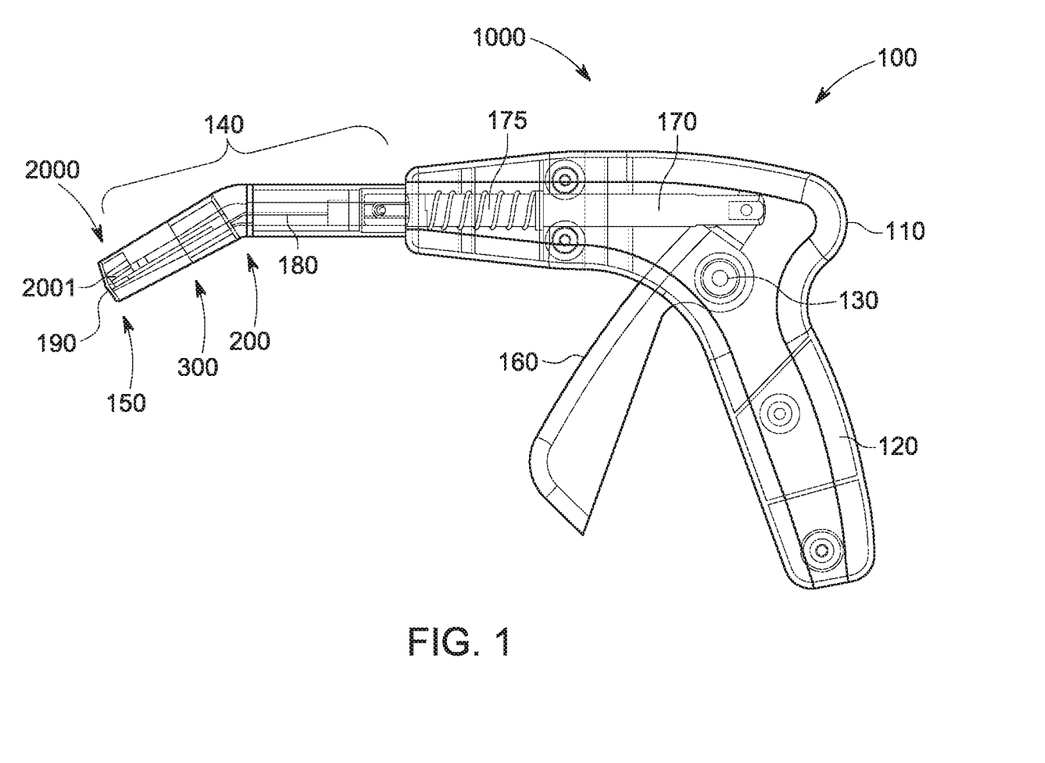
FIG. 1 shows a side semi-transparent view of an embodiment of the surgical intraoral stapling apparatus.

Referring now to FIG. 1, there is shown a side semi-transparent view of an embodiment of the surgical intraoral stapling apparatus. The surgical intraoral stapling apparatus 1000 generally provides an elongated housing having a free forward end, a surgical staple slidable longitudinally within the housing towards the forward end thereof, a staple firing mechanism for loading, advancing, and firing the surgical staple towards the forward end, biasing the surgical staple to a staple open biasing position by bending a pair of free bias arms of the surgical staple away from each other and releasing the staple at a suturing tissue site.

In the illustrative embodiment, the surgical intraoral stapling apparatus 1000 comprises a handle assembly 100 at a rearward end 160 thereof, wherein the handle assembly 100 comprises a movable trigger 110 and a fixed handle 120. The movable trigger 110 is pivotally affixed to the fixed handle 120 via one or more pivotable connectors 130 that provide for relative motion of the movable trigger 110 toward and away from the fixed handle 120. The trigger 110 is operably connected to a transmission shaft (or actuation rod) 170 disposed within the handle assembly 100. The transmission shaft 170 and trigger 110 form a mechanical connection that provides for controlled actuation of both components.

In the shown embodiment, the surgical intraoral stapling apparatus 1000 provides for single hand actuation of the trigger 110, and therefore the transmission shaft 170. In an alternative embodiment, the trigger 110 is an automated action assisted partially or completely by a motor or actuator. In the shown embodiment, a transmission shaft spring 175 is operably connected to the transmission shaft 170 and biases the transmission shaft 170 to return to an initial retracted position, whereby the transmission shaft 170 is positioned to the rearward end 160 of the surgical intraoral stapling apparatus 1000. In alternative embodiments, the transmission shaft spring 175 biases the transmission shaft 170 in the opposing position.

A barrel section 140 extends outward from the handle assembly 100, wherein the barrel section 140 generally includes an elongated shape that allows for surgical staples to be applied to difficult-to-reach locations within a patient's oral cavity. The barrel section 140 houses a staple firing mechanism 200, an advancing unit 300, a bar 180, and the surgical staples 2000 therein. The staple firing mechanism 200 and advancing unit 300 cooperatively provides for the loading and advancement of the surgical staples 2000.

In the shown embodiment, the transmission shaft 170 comprises a cylindrical rod extending linearly from the rearward end 160 to the forward end 150. Actuation of the trigger 110 causes the transmission shaft 170 to move in a linear direction to extend and retract from the handle assembly 100 into the barrel section 140, where the transmission shaft 170 is operably connected to the bar 180. The pivotable connector 130 of the handle assembly 100 is configured such that when the movable trigger 110 is actuated, the transmission shaft 170 is placed into a substantially collinear or aligned position with the bar 180 when it is moved forward to contact the bar 180, thereby causing the distal end of the transmission shaft 170 to engage the proximal end of the bar 180. This minimizes the lateral forces exerted on the bar 180 and ensures that the bar 180 travels in a substantially linear direction when contacted.

In the shown embodiment, barrel section 140 of the surgical intraoral stapling apparatus 1000 is hollow and angled downward from the handle assembly 100 to permit the operator to see when the forward end 150 has been brought in close proximity to the selected tissue site for suturing. The forward end 150 of the surgical intraoral stapling apparatus 1000 provides a planar front side having an open slot 190 disposed thereon and facing the forward end 150. The open slot 190 is dimensioned to provide the passing of the surgical staples 2000 therethrough.

In the shown embodiment, the surgical staples 2000 are prearranged within the barrel section 140 in such a way that the single, lowermost staple 2001 is the only staple 2000 configured to engage the advancing unit 300. The surgical staples 2000 are oriented horizontally flat, having the free arms of each staple oriented towards the forward end 150 and vertically stacked atop each other. The prearranged staples 2000 are positioned within a staple cartridge 2100 that is generally integrated into the barrel section 140. The staple cartridge may further provide a staple spring 2060 disposed therein that biases the prearranged staples 2000 downward towards the advancing unit 300. In this way, once the lowermost staple 2001 has been loaded, advanced, and fired, the next lowermost staple will occupy that lowermost position and be primed to engage the advancing unit 300 upon the return to the loading position, thereby providing for repeat cycles of loading, advancing, and firing the lowermost staple 2001.

In the illustrated embodiment, the bar 180 includes an angled portion that generally equals the downward angle of the barrel section 140. In this way, the bar 180 linearly bears against the transmission shaft 170 at the proximal end and linearly engages the advancing unit 300 at the distal end thereof. An exemplary bar 180 is generally elongated in the longitudinal direction and thin. In some embodiments, the bar 180 is stamped from a thin sheet of metal or other material or may be otherwise fabricated, in alternate embodiments.

In the shown embodiment, the handle assembly 100 and barrel section 140 form separate structures and substructures that are semi-permanently joined to form the assembled surgical intraoral stapling apparatus 1000. In this context, the semi-permanent joining requires the use of a tool, such as a screwdriver, for the separation of the structures for repair or replacement. However, in alternative embodiments, the handle assembly 100 and barrel section 140 form a single integral and monolithic structure to which the trigger is actuatable.

Figure 2:
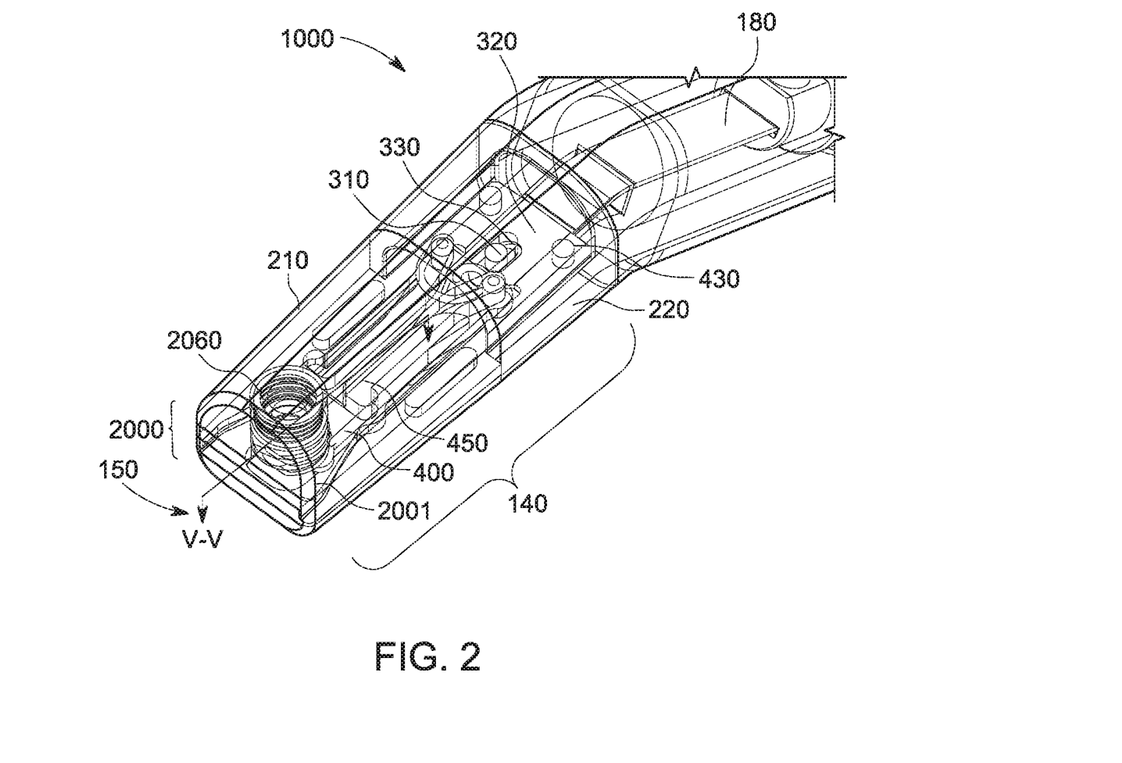
FIG. 2 shows a perspective semi-transparent view of a forward end of an embodiment of the surgical intraoral stapling apparatus in the loading position.
Figure 4:
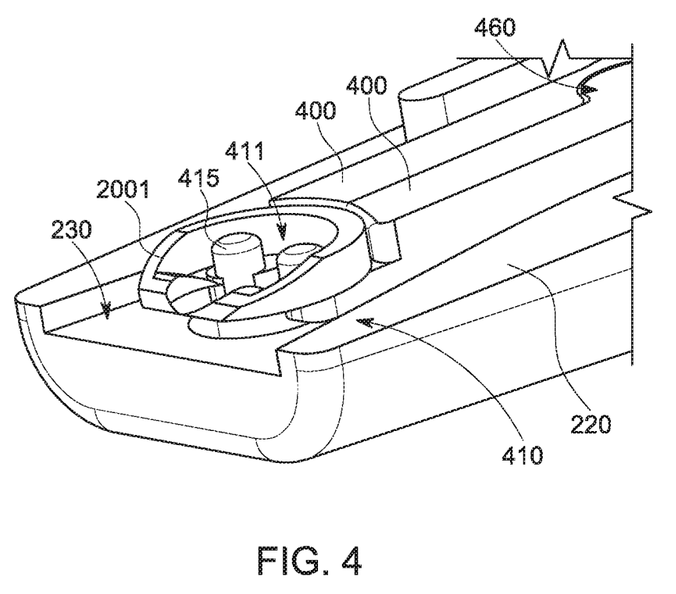
FIG. 4 shows a close-up view of an embodiment of the surgical intraoral stapling apparatus.
Figure 5:
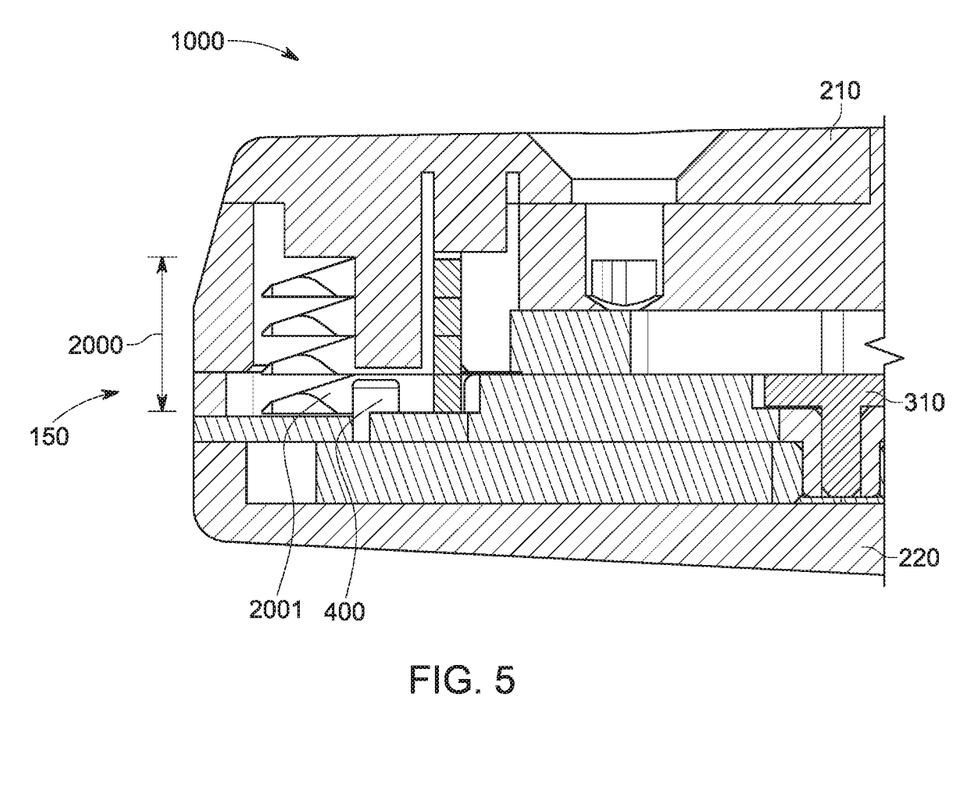
FIG. 5 shows a cross sectional view of an embodiment of the surgical intraoral stapling apparatus taken along line V-V of FIG. 2.

Referring now to FIGS. 2 and 5, there is shown a perspective semi-transparent view of a forward end of an embodiment of the surgical intraoral stapling apparatus in the loading position and a cross sectional view of an embodiment of the surgical intraoral stapling apparatus taken along line V-V of FIG. 2, respectively. The forward end 150 of the surgical intraoral stapling apparatus 1000 comprises the barrel section 140 having the staple firing mechanism 200. The staple firing mechanism 200 comprises a fixed body 220 that forms a lower portion of the barrel section 140. The fixed body 220 forms a channel 230 within the barrel section 140 adapted to receive the advancing unit 300 therein. In the shown embodiment, the fixed body 220 comprises a U-shaped member that stretched between the underside of the barrel section 140 and extends partially upward along the opposing lateral sides thereof. The channel 230 (best seen in FIG. 4) formed by the shape of the fixed body 220 is configured to allow the advancing unit 300 to slide back and forth therein, driven by the bar 180. In some embodiments, the barrel section 140 further comprises a removable staple housing 210 disposed along an upper end thereof. The staple housing 210 includes a U-shaped covering that secures to the fixed body 220 via a pair mating fasteners 250. In the illustrated embodiment, the staple housing includes a female portion of the mating fastener and the fixed body 220 comprises a male portion.

The advancing unit 300 is operably connected to the bar 180 via a driving pin 310, wherein the bar 180 is operably connected to the transmission shaft and configured to slide the advancing unit 300 relative the fixed body 220. In the illustrated embodiment, the advancing unit 300 comprises a sliding plate 320 having a centrally disposed aperture 330, wherein the driving pin 310 extends upwards therethrough. (See FIGS. 6 and 7).

The advancing unit 300 further comprises a pair of splay arms 400 disposed forward the sliding plate 320 and generally oriented longitudinally along the barrel section 140. Each arm of the pair of splay arms 400 comprises an elongated member having a forward end 410 opposite a rearward end 420, wherein the rearward end 420 comprising a vertical pivot pin 430 extending from an upper side of each splay arm 400 and into a track 450 disposed on the upper end of the barrel section 140. In the illustrated embodiment, the upper end of the barrel section is opposite the U-shaped fixed body 220.

The track 450 is configured to slidably receive the pivot pin 430 therein. As seen in FIG. 2 (wherein the advancing unit 300 is in the loading position) and FIG. 6 (wherein the advancing unit 300 is in the forward advancing position), the track 450 guides the pair of splay arms 400 therealong, as the loading, advancing, and firing of the surgical intraoral stapling apparatus 1000 cycles through the positions.

As stated above, the pair of splay arms 400 are positioned in the loaded position in FIGS. 2 and 5, wherein staple spring 2060 positions the staples 2000 to be engaged with the pair of splay arms 400. Specifically referring to FIG. 5, the staples 2000 are seen positioned above the pair of splay arms 400 and adapted to load or otherwise engage the lowermost staple 2001 to the splay arms 400. As the splay arms 400 advance forward, the next lowermost staple of the staples 2000 rests atop an upper surface of the splay arms 400. In the illustrated embodiment, the staple spring 2060 extends into the channel 230 from the upper end of the barrel section 140.

Figure 3:
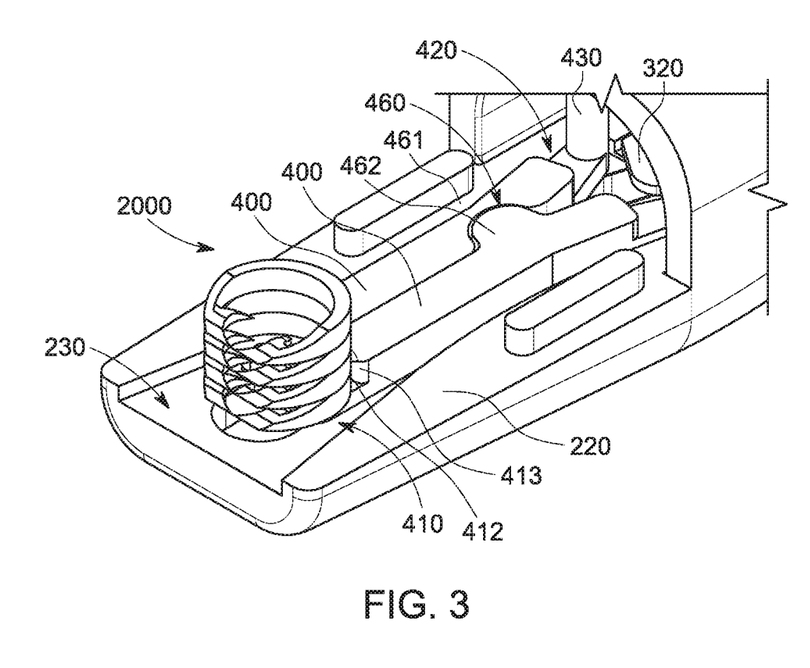
FIG. 3 shows a perspective semi-transparent view of the forward end of an embodiment of surgical intraoral stapling apparatus with the staple housing removed.

Referring now to FIGS. 3 and 4, there is shown a perspective semi-transparent view of the forward end of an embodiment of surgical intraoral stapling apparatus with the staple housing removed and a close-up view of an embodiment of the surgical intraoral stapling apparatus, respectively. In the shown embodiment, the pair of splay arms 400 are disposed and ride along the surface of the channel 230 of the fixed body 220.

Each arm of the pair of splay arms 400 comprises a forward end 410 and a rearward end 420. The forward end 410 comprising a recessed portion 411 forming an upper side 412 and a sidewall 413 facing the forward end 410, wherein a protruding stud 415 extends from the upper side 412 thereof. The protruding stud 415 is configured to extend into an interior region of the staple and the sidewall 413 is configured to abut and bear against an exterior side of the staple 2000, whereupon actuation of the trigger, the protruding stud and the sidewall are configured to cooperatively load, advance, and open the staple for suture. In the shown embodiment, the protruding stud 415 is cylindrical. However, in alternative embodiments, the dimension and geometry of the protruding stud 415 may have various shapes to compliment the dimension and geometry of the staple. In the shown embodiment, the height of the splay arms 400 is generally equal to the height of each of the staples 2000. In this way, as the lowermost staple is loaded into the splay arms 400, the next lowest staple remains in a position to replace the now loaded staple upon the return of the splay arms 400 into the loading position. During the cycling between a first loading position and a second loading position, the next lowermost staple rests atop an upper surface of the splay arms between the forward end 410 and the rearward end 420 thereof. As seen in FIG. 5, the splay arms 400 have a thickness generally equal to the thickness of the staple 2000. Additionally, the upper surface of the splay arms 400 is planar so as to permit sliding between the splay arms 400 and the next lowermost staple, even as the next lowermost staple is biased into the upper surface of the splay arms 400 by the staple spring 2060 (shown in FIG. 2).

In the illustrated embodiment, the pair of splay arms 400 comprise a mating engagement member 460 intermediate the forward end 410 and the rearward end 420, wherein the mating engagement member 460 is disposed on each arm 400. The mating engagement member 460 is configured to provide relative rotational movement of each of the splay arms 400 at the forward end 410. In the shown embodiment, a first arm 400 comprises a mating depression 461 and a second arm 400 comprises a mating tab 462, wherein the mating depression and tab 461, 462 are complimentary. The cross section of the mating depression and tab 461, 462 are semi-circular, and are configured to provide rotation between the splay arms 400, provided the space either forward or rearward the mating depression and tab 461, 462. As seen in FIG. 3, directly rearward of the mating depression and tab 461, 462, each of the splay arms flare outward from the mating engagement member 460. In this way, should the rearward end 420 of the pair of splay arms 400 be moved towards each other, the mating engagement member 460 would provide rotation thereabout, and cause the forward end 410 of the pair of splay arms 400 to rotate counter (away from each other).

Specifically referring to FIG. 3, the pivot pin 430 extends directly from the rearward end 420 of each of the splay arms 400. The pivot pin 430 is operably connected to the sliding plate 320, such that the sliding plate 320 is configured to advance the pair of splay arms 400 along the channel cause 230 and cause the forward end 410 of the arms 400 to eventually move away from each other.

Figure 6:
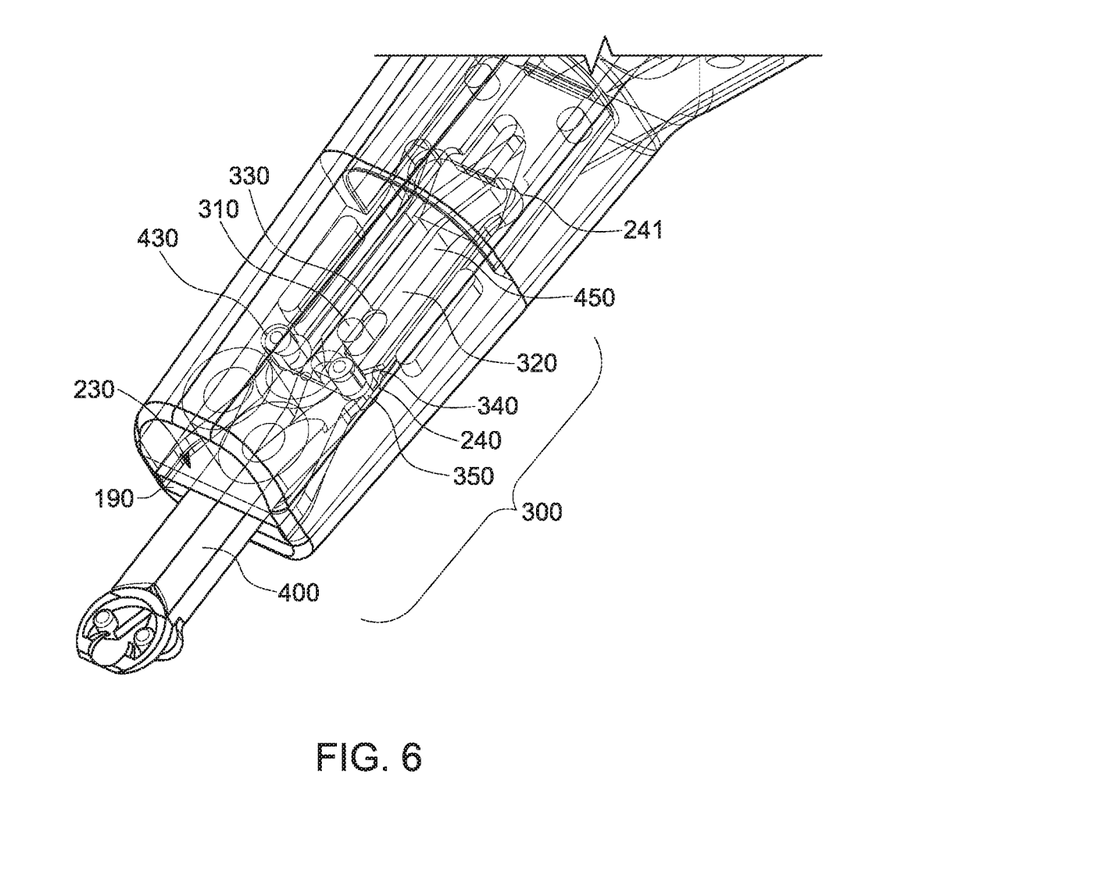
FIG. 6 shows a perspective semi-transparent view of the forward end of an embodiment of the surgical intraoral stapling apparatus in the advanced position.
Figure 7:
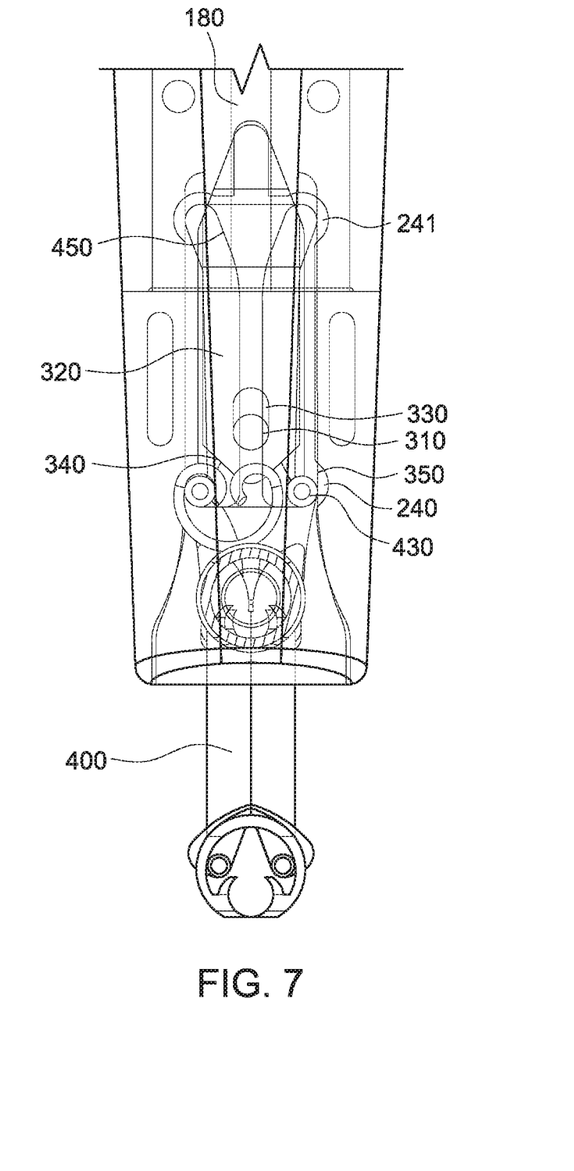
FIG. 7 shows an overhead semi-transparent view of the forward end of an embodiment of the surgical intraoral stapling apparatus in the advanced position.

Referring now to FIGS. 6 and 7, there are shown a perspective semi-transparent view of the forward end of an embodiment of the surgical intraoral stapling apparatus in the advanced position and an overhead semi-transparent view of the forward end of an embodiment of the surgical intraoral stapling apparatus in the advanced position, respectively. In the illustrated embodiments, the advancing unit 300 is in the forward advanced position. The sliding plate 320 is disposed within the channel 230 and interconnected to the bar 180 via a driving pin 310 extending through the aperture 330 of the sliding plate. In contrast to the loading position (FIG. 2), in the forward advance position the pair of splay arms 400 extend past the front side and through the open slot 190. Additionally, the driving pin 310, the splay arms 400, and the pivot pins 430 are shown disposed forward, relative to the loading position.

In this forward advancing position, the sliding of the bar 180 causes the driving pin 310 to bear against an interior of the aperture 330, wherein the bar 180 is configured to cause cooperate movement of the sliding plate 320 and the pair of splay arms 400. In the shown embodiment, the sliding plate 320 comprises an angled leading edge 340 that extends forward at the centerline and tapers from the centerline to both lateral opposing sides thereof. The sliding plate 320 is disposed generally horizontal relative to the pivot pins 430, such that the angled leading edge 340 of the sliding plate 320 causes engage with the pivot pins 430 along the tapered portions of the angled leading edge 340. Additionally, the pivot pins 430 are seen here in a forwardmost position in the track 450. In the shown embodiment, the track 450 is shown as being generally longitudinal along the barrel section.

In the shown embodiment, the pair of splay arms 400 comprises a bulbous region 350 disposed towards the rearward end 420, wherein each of the splay arms 400 flare outward from the mating engagement member 460 (shown in FIG. 3) to the rearward end 420. The bulbous region 350 is configured to engage a complimentary detent region 240 of the channel 230. The channel 230 forms the complimentary detent region 240 on opposing lateral sides thereof, such that each detent 240 extends into the fixed body 220. In this way, as the bulbous region 350 of the pair of splay arms 400 slide forward, the tapered portions of the angled leading edge 340 permits the bulbous region 350 to become secured within the complimentary detent region 240 and cease any further forward movement reaching the forward advancing position. In the shown embodiment, the track comprises a second detent region 241 that receives the bulbous region 350 in the loading position Referring now to FIGS. 8 and 9, there is shown a perspective view of the forward end of an embodiment of the surgical intraoral stapling apparatus in the staple open biasing position, and there is shown a perspective view of an embodiment of the surgical intraoral stapling apparatus being used to apply a staple to a wound site, respectively.

Figure 8:
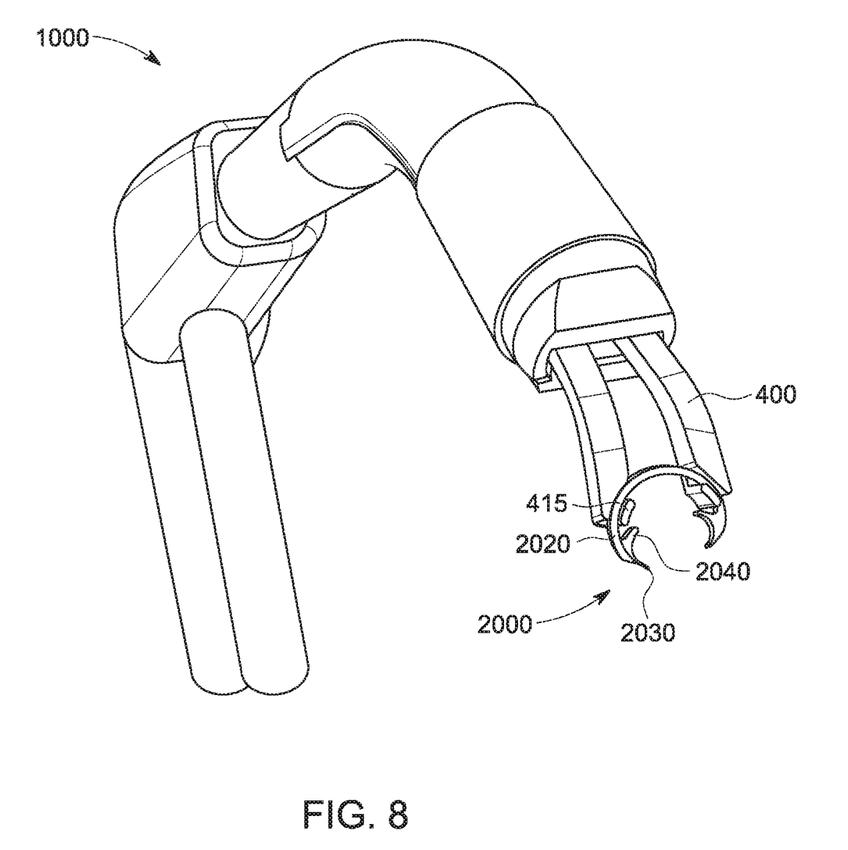
FIG. 8 shows a perspective view of the forward end of an embodiment of the surgical intraoral stapling apparatus in the staple open biasing position.

In the shown staple biasing position, the surgical intraoral stapling apparatus 1000 is fully actuated and the staple 2000 is ready to be sutured to a tissue site. In this embodiment, the staple 2000 comprises a pair of biased arm members 2020 arranged in a semi-circular configuration, a pair of pointed ends 2030 disposed at the distal ends of the biased arm members 2020, and a pair of in-turned protrusions 2040 extending inwardly from a point along the length of the arm members 2020. The pair of biased arm members 2020 arranged in a semi-circular configuration form an exterior sidewall extending circumventially about the staple 2000, wherein the sidewall of the staple 2000 is configured to provide a surface the engage the sidewall of each of the splay arms 400. The pair of in-turned protrusions 2040 are configured to fit and receive the protruding studs 415 of each of the splay arms 400. The pointed ends 2030 and the protrusions 2040 are arranged in a generally perpendicular relationship to each other. When the staple 2000 is in its closed position, as depicted in FIGS. 6 and 7, the pointed ends 2030 of the staple 2000 are in contact, forming a temporarily closed loop. In one embodiment, the staples 2000 have a thickness generally equal to the thickness of the splay arms 400. In alternative embodiments, the staples 2000 have a thickness less than that of the splay arms 400.

When a staple 2000 has been ejected or fired and is positioned within the splay arms in the staple open biasing position, the staple 2000 is ready to be applied to the tissue site. The operator can selectively position the pointed ends 2030 of the bias arms 2020 of the staple 2000 so that the arm members 2020 are positioned around the tissue site. The elongated nature of the arm members 2020, in combination with the elongated barrel section 140, allows for the staple 2000 to be applied at any point within the oral cavity of the patient in a convenient manner.

Figure 9:
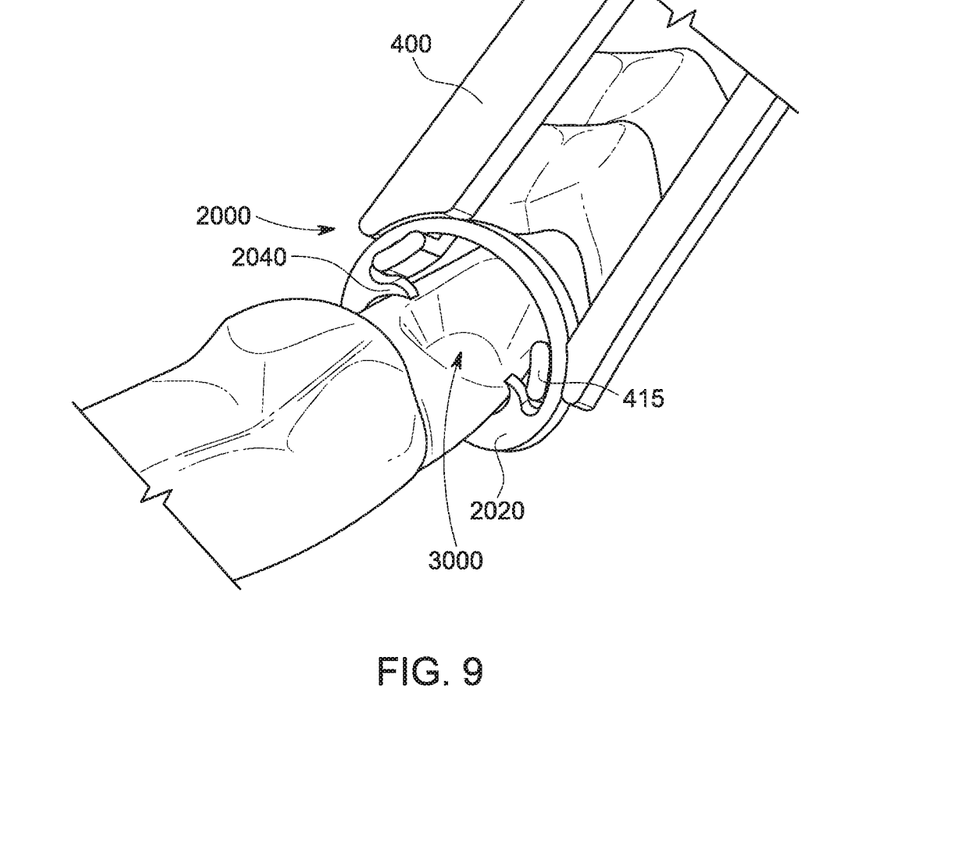
FIG. 9 shows a perspective view of an embodiment of the surgical intraoral stapling apparatus being used to apply a staple to a wound site.

Once the staple 201 is positioned over the wound site 501, the operator can then move the stapler 2000 so that the arm members 2020 are angled downwardly, pulling the protrusions 2040 of the staple 2000 over the sides of the wound site 3000. The staple 201 can be pulled across the wound site 3000 via the pair of splay arms 400 in which the staple 2000 is resting. Once the staple 2000 is positioned over the wound site 3000, the trigger is released and the splay arms 400 begin to move towards each other. Once the trigger is released (effectively firing the staple), the biasing of the staple 2000 causes the arm members 2020 to close, suturing the wound site 3000 closed via pressure from the arm members 2020 thereagainst.

Referring to FIG. 2 (loading position), FIGS. 6 and 7 (forward advanced position) and FIG. 8 (staple biasing position), the surgical intraoral stapling apparatus 1000 is seen cycling through the positions for loading, advancing, and firing the staple 2000. The advancing unit 300 is slidably disposed within the fixed body 220, wherein the advancing unit is selectively movable between a loading position, a forward advancing position, and a staple open biasing position.

In the illustrated embodiment, in the loading position, the pair of splay arms 400 are entirely disposed within the barrel section 140, and the staples 2000 are positioned within the staple cartridge 2100 disposed atop the pair of splay arms 400 and engaged therewith. The protruding stud 415 of each of the splay arms 400 are positioned within the lowermost staple 2001, and as the trigger is actuated, a transition between the loading position and the forward advancing position occurs. During this transition, the sliding plate 320 moves forward and bears against the pair of splay arms 400 to cause cooperative forward movement. The pivot pins 430 of the splay arms 400 travel along the track 450 until a forwardmost position is reached, wherein the pivot pins 430 to fit a pair of lateral cutouts configured to receive the pivot pins 430. In this forwardmost position, the bulbous region 350 simultaneously engages the complimentary detent region 240 of the channel 230. Additionally, when the splay arms 400 have reached the forwardmost position, the forward end 410 of the splay arms 400 and the engaged staple 2000 are positioned through the open slot 190 and outside the barrel section 140.

During transition between the forward advancing position and the staple biasing position, the further actuation of the trigger causes the forward end 410 of the splay arms 400 to move away from each other, thereby opening the free bias arm members 2020 of the staple 2000. In one embodiment, the channel 230 of the fixed body 220 expands in width towards the forward end 410, such that the pair of splay arms 400 are permitted to move away from each other in the between the forward advancing position and the staple open biasing position. Further, the channel 230 is configured to abut the pair of splay arms 400 in an openmost staple open biasing position. The widening of the channel 230 and the mating engagement members 460 cooperatively permits each of the splay arms 400 to move away from the other arm, and therefore also configured to form a gap between a pair of biased arm members 2020 of the loaded staple 2000. In one embodiment, the angled leading edge 340 of the sliding plate 320 moves forward to engage the pins disposed within the complimentary detent region 240 of the channel 230. As the angled leading edge 340 advances forward, the angled engagement therebetween causes a torque on the pivot pin 430, causing the pivot pin 430 to rotate within the detent region 240. This rotation at the rearward end of the splay arms, causes an opposing rotation at the forward end, thereby moving each of the splay arms 400 away from each other.

In one embodiment, a splay arm spring 480 is operably connected to the splay arms 400 and is configured to bias the splay arms 400 towards each other. In the shown embodiment, the arm spring 480 is positioned about one of the pivot pins 430 of the splay arms 400, and thereby provide a torque that suggests to close the splay arms 400.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. An intraoral surgical stapling apparatus, comprising:
   a handle assembly having a trigger configured for selective actuation of a surgical staple of the intraoral surgical stapling apparatus;
   a barrel section extending outward from the handle assembly, the barrel section including a staple firing mechanism configured to load and advance the surgical staple in a loading position towards a forward end of the intraoral surgical stapling apparatus;
   the staple firing mechanism comprising a fixed body forming a channel, the channel adapted to receive an advancing unit therein, the advancing unit operably connected to the trigger;
   the advancing unit comprising:
      a sliding plate disposed within the channel;
      a pair of splay arms positioned forward the sliding plate, wherein each of the splay arms comprise:
         a forward end opposite a rearward end, the rearward end comprising a vertical pivot pin extending from an upper side thereof and extending into a track disposed along an upper end of the barrel section, the track configured to slidably receive the pivot pin therein;
         the forward end comprising a recessed portion configured to engage the surgical staple;
         wherein a forwardmost portion of the track prevents further advancement of the pivot pin;
         wherein actuation of the trigger is configured to cause cooperate movement of the sliding plate and the pair of splay arms;
   wherein the advancing unit is selectively movable between the loading position, a forward advancing position, and a staple open biasing position;
   wherein the loading position, the advancing unit is configured to engage the staple;
   wherein the forward advancing position, the pair of splay arms are advance the engaged staple forward;
   wherein the staple open biasing position, the engaged staple is biased and configured to be applied to the tissue site.

2. The intraoral surgical stapling apparatus of claim 1, wherein the trigger is pivotally affixed to a fixed handle of the handle assembly, the trigger configured to selectively actuate for loading, advancing, and suturing a staple at a tissue site.

3. The intraoral surgical stapling apparatus of claim 1, wherein the barrel section further comprises a removable staple housing having a staple cartridge disposed on an upper side thereof.

4. The intraoral surgical stapling apparatus of claim 3, wherein the staple cartridge is configured to house the surgical staples vertically stacked and oriented forward.

5. The intraoral surgical stapling apparatus of claim 4, wherein the staple cartridge comprises a staple spring disposed therein, the staple spring configured to biases the surgical staples downward towards the advancing unit in the loading position.

6. The intraoral surgical stapling apparatus of claim 1, wherein the recessed position of each of the splay arms form an upper side and a sidewall facing the forward end, wherein a protruding stud extends from the upper side thereof, wherein the protruding stud is configured to extend into an interior region of the staple and the sidewall is configured to abut and bear against an exterior side of the staple, whereupon actuation of the trigger the protruding stud and the sidewall are configured to cooperatively load, advance, and open the staple for suture.

7. The intraoral surgical stapling apparatus of claim 1, wherein each of the splay arms further comprise a mating engagement member intermediate the forward end and the rearward end, wherein the mating engagement member is configured to provide relative rotational movement of each of the splay arms at the forward end.

8. The intraoral surgical stapling apparatus of claim 7, wherein each of the splay arms further comprise a bulbous region disposed towards the rearward end, wherein each of the splay arms flare outward from a mating engagement member, wherein bulbous region is configured to engage a complimentary detent region of the channel.

9. The intraoral surgical stapling apparatus of claim 8, wherein the channel forms the complimentary detent on opposing sides thereof such that each detent extends into the sidewall of the fixed body.

10. The intraoral surgical stapling apparatus of claim 9, wherein the forwardmost portion of the track includes a lateral cutout configured to receive the pivot pin.

11. The intraoral surgical stapling apparatus of claim 10, wherein the pair of bulbous regions and the pivot pins form a semi-permanently fixed position to prevent any further advancement of the pair of splay arms towards the forward end when advanced by the angled leading edge to fit within the complimentary detent and lateral cutout, respectively.

12. The intraoral surgical stapling apparatus of claim 1, wherein the loading position, the pair of splay arms are entirely disposed within the barrel section, and wherein the staple is positioned within the recessed portion of each arm of the pair of splay arms.

13. The intraoral surgical stapling apparatus of claim 1, wherein transition between the loading position and the forward advancing position causes the sliding plate to bear against the pair of splay arms to cause cooperative forward movement.

14. The intraoral surgical stapling apparatus of claim 1, wherein the sliding plate comprises an angled leading edge that tapers from a centerline to both lateral opposing sides thereof.

15. The intraoral surgical stapling apparatus of claim 1, wherein transition between the forward advancing position and the staple biasing position causes the pair of splay arms to be semi-permanently fixed to the channel via the pivot pins, wherein further actuation of the trigger is configured to causes a torque to be applied to each pivot pin, and, in cooperation with the mating engagement member, cause each of the splay arms to move away from the other arm, and therefore also configured to form a gap between a pair of biased arm members of the engaged staple.

16. The intraoral surgical stapling apparatus of claim 15, wherein the sliding plate comprises an angled leading edge that tapers from a centerline to both lateral opposing sides thereof, the angled leading edge configured to apply the torque to each pivot pin.

17. The intraoral surgical stapling apparatus of claim 1, further comprising a transmission shaft connecting the trigger to a bar, the transmission shaft configured for sliding translation along a longitudinal axis of the stapler, wherein the bar extends longitudinally along the intraoral surgical stapling apparatus, wherein a transmission shaft spring is operably connected to the transmission shaft and biases the transmission shaft to return to an initial retracted position.

18. The intraoral surgical stapling apparatus of claim 1, wherein the bar comprises a driving pin extending through an aperture of the sliding plate, wherein the sliding of the bar causes the driving pin to bear against an interior of the aperture and wherein the bar is configured to cause cooperate movement of the sliding plate, the pair of splay arms, and the bar.

19. The intraoral surgical stapling apparatus of claim 1, further comprising a splay arm spring operably connected to the splay arms and is configured to bias the splay arms towards each other.

20. The intraoral surgical stapling apparatus of claim 1, wherein a single actuation of the trigger is configured to cycle through the loading position, the forward advancing position, and the staple open biasing position.

* * * * *